United States Patent [19]

McGuire et al.

[11] Patent Number: 5,391,170
[45] Date of Patent: Feb. 21, 1995

[54] ANGLED SURGICAL SCREW DRIVER AND METHODS OF ARTHROSCOPIC LIGAMENT RECONSTRUCTION

[75] Inventors: David A. McGuire, 3418 Lakeside Dr., Anchorage, Ak. 99515; Steven Ek, Bolton, Mass.; Sam R. Marchand, Dunedin; Matthew R. Frushell, Clearwater, both of Fla.

[73] Assignee: David A. McGuire, Anchorage, Ak.

[21] Appl. No.: 956,733

[22] Filed: Oct. 2, 1992

Related U.S. Application Data

[63] Continuation-in-part of Ser. No. 806,906, Dec. 13, 1991, Pat. No. 5,257,996, and a continuation-in-part of Ser. No. 839,466, Feb. 19, 1992.

[51] Int. Cl.$^6$ .......................... A61F 5/00; A61F 2/32; A61F 2/08; A61F 2/44
[52] U.S. Cl. ........................................ 606/86; 606/88; 606/104; 623/13; 623/17
[58] Field of Search .............. 606/61, 72, 73, 75, 606/76, 77, 86, 87, 88, 96, 97, 98, 104; 623/13, 17

[56] References Cited

U.S. PATENT DOCUMENTS

| | | | |
|---|---|---|---|
| 877,571 | 1/1908 | Larson | 81/57.29 |
| 933,639 | 9/1909 | Frink . | |
| 1,199,823 | 10/1916 | Sadtler . | |
| 1,398,116 | 11/1921 | Root . | |
| 1,428,282 | 9/1922 | Glabaznya . | |
| 2,042,376 | 5/1936 | Balga | 279/89 |
| 2,267,925 | 12/1941 | Johnston | 128/92 |
| 2,570,465 | 10/1951 | Lundholm | 128/92 |
| 3,232,151 | 2/1966 | Blachowski | 81/177 |
| 3,351,054 | 11/1967 | Florek | 128/83 |
| 3,696,694 | 10/1972 | Boro | 81/57.27 |
| 3,788,169 | 1/1974 | Nakayama | 81/177 UJ |
| 3,892,232 | 7/1975 | Neufeld | 128/92 |
| 4,140,111 | 2/1979 | Morrill | 128/92 E |
| 4,381,770 | 5/1983 | Neufeld | 128/92 BA |
| 4,383,527 | 5/1983 | Asnis et al. | 128/92 EB |
| 4,441,563 | 4/1984 | Walton, II | 173/163 |
| 4,450,835 | 5/1984 | Asnis et al. | 128/92 EB |
| 4,620,458 | 11/1986 | Schmidek | 81/57.28 |
| 4,643,052 | 2/1987 | Badiali | 81/57.28 |
| 4,712,542 | 12/1987 | Daniel et al. | 623/13 |
| 4,738,255 | 4/1988 | Goble . | |
| 4,772,286 | 9/1988 | Goble et al. | 623/13 |
| 4,781,182 | 11/1988 | Purnell et al. | 128/92 VD |
| 4,834,752 | 5/1989 | Van Kampen | 623/13 |
| 4,894,063 | 1/1990 | Nashef | 623/13 |
| 4,927,421 | 5/1990 | Goble et al. | 606/73 |
| 4,932,972 | 6/1990 | Dunn | 623/13 |
| 4,947,942 | 8/1990 | Lightle et al. | 173/163 |
| 4,950,270 | 8/1990 | Bowman et al. | 606/72 |
| 5,041,119 | 8/1991 | Frigg et al. | 606/96 |
| 5,069,569 | 12/1991 | Lieser | 403/57 |
| 5,139,520 | 8/1992 | Rosenberg | 623/13 |
| 5,152,790 | 10/1992 | Rosenburg | 623/13 |
| 5,281,422 | 1/1994 | Badylack | 623/13 |
| 5,314,429 | 5/1994 | Goble | 606/88 |
| 5,320,115 | 6/1994 | Kenna | 623/13 |

FOREIGN PATENT DOCUMENTS 645252 of 0000 Canada .

OTHER PUBLICATIONS

Burnett and Fowler; *Reconstruction of the Anterior Cruciate Ligament: Historical Overview,* Jan. 1985, Orthopedic Clinics of North America, vol. 16, No. 1, pp. 143-157.

*Technique for Endoscopic Patellar Tendon Bone Block Fixation Using a Cannulated Interference Screw System.*
Statak; *Soft Tissue Attachment Device,* by Zimmer, Inc. 1988.

*Primary Examiner*—Michael A. Brown
*Attorney, Agent, or Firm*—Bromberg & Sunstein

[57] ABSTRACT

A surgical screw driver for inserting bone screws in bone tunnels in ligament reconstruction has, in a preferred embodiment, a rotatable operating shaft disposed at an angle to a drive shaft. A mechanism is on the drive shaft for retaining a bone screw. Methods of arthroscopic cruciate ligament reconstruction include the steps of introducing a surgical screw driver through a portal that is offset from the longitudinal axis of a bone tunnel and driving a bone screw mounted on the driver in the bone tunnel to fixate a bone block in the bone tunnel.

22 Claims, 4 Drawing Sheets

ANGLED SURGICAL SCREW DRIVER AND METHODS OF ARTHROSCOPIC LIGAMENT RECONSTRUCTION

This application is a continuation-in-part of applications Ser. No. 07/806,906, filed Dec. 13, 1991, U.S. Pat. No. 5,257,996, for an invention entitled "Surgical Pim Passer" and Ser. No. 07/839,466, filed Feb. 19, 1992, for an invention entitled "Femoral Guide and Methods of Precisely Forming Bone Tunnels in Cruciate Ligament Reconstruction of the Knee." These related applications are hereby incorporated herein by reference.

TECHNICAL FIELD

The present invention pertains to surgical screw drivers for inserting bone screws and, more particularly, to surgical screw drivers for inserting interference bone fixation screws in bone tunnels and to methods of performing arthroscopic cruciate ligament reconstruction of the knee.

BACKGROUND ART

Various surgical procedures utilize devices to fixate anatomical tissue for healing. An example of a fixation device is an interference bone fixation screw, commonly referred to throughout the present description as "bone screw", used to fixate ligaments within bone tunnels during cruciate ligament reconstruction of the knee.

A surgical screw driver is commonly used to insert bone screws. This form of screwdriver has a rotatable drive shaft for rotating the screw, and advancing it along the longitudinal axis of the driver. The driver cooperatively engages with a drive recess, within the bone screw, to help achieve axial alignment of the screw with the drive shaft of the screw driver.

In cruciate ligament reconstruction, the bone screw is inserted into tandem isometrically positioned bone tunnels formed in the tibia and femur. A prosthetic ligament graft affixed to bone blocks at each end is inserted into the bone tunnel such that the ligament extends across the knee joint in the anatomical position of the cruciate ligament. The bone blocks are fixated within the bone tunnel by bone screws. Each bone screws is inserted in the bone tunnel so as to be disposed laterally between the walls of the bone tunnel and the bone block. Successful cruciate ligament reconstruction depends on the proper insertion of the bone screw along the longitudinal axis of the bone tunnel, parallel to both the tunnel walls and the bone block. Incorrect insertion of the bone screw causes screw divergence, resulting in increased difficulty in advancing the screw in the bone tunnel and reduced contact between the threads on the screw and the bone block. In addition, screw convergence can result in crushing or fracturing of the ligament and dislocation of the bone block, causing deviation of the ligament from an accurate, pre-established isometric position.

Cruciate ligament reconstruction is commonly performed as an open surgical procedure. Incisions on the order of 10 inches in length are utilized to access the knee joint. These relatively long incisions are required to provide room for the surgical screw driver to approach the tibial and femoral bone tunnels from directions aligned with the longitudinal axes of the bone tunnels and thereby to permit the driver to drive the bone screws effectively in a direction parallel with the bone block and the walls of the bone tunnels.

Open surgery possesses numerous disadvantageous compared to closed surgery or less invasive (arthroscopic) surgery for ligament reconstruction. These disadvantages include possible violation of mechanoreceptors in the knee, dessication of articular cartilage of the joint, increased tissue trauma resulting from incisions accompanied by increased patient discomfort and delayed post surgical mobility. In addition, hospitalization and rehabilitation times may be prolonged.

Accordingly, it is desirable to develop methods for performing cruciate ligament reconstruction that are less invasive, such as arthroscopic surgical procedures. Narrow portals are made with a puncture or stab wound in tissue adjacent to the knee of sufficient size to permit insertion of surgical instruments at the knee joint with the knee being visualized with an arthroscope. An arthroscope is here defined as any instrument for insertion into the cavity of a joint in order to inspect its contents. An example of an arthroscope is a fiberscope, which uses fiber optics to transmit images from the interior of the joint.

A method of arthroscopic cruciate ligament reconstruction can provide many benefits over open surgery, including reduced tissue trauma, decreased patient discomfort, earlier and aggressive range of motion and weight bearing without loss of fixation, reduced rehabilitation time and elimination of hospitalization because the procedures can be performed on an out-patient basis.

The limitations on maneuverability imposed by arthroscopic cruciate ligament reconstruction and the location of the arthroscopic portals in tissue adjacent to the knee mean that conventional drivers with straight drive shafts, which are used for placing bone screws into bone tunnels through incisions during open surgery, are not suited for this procedure.

Indeed, the anteromedial and anterolateral portals are angularly offset from the longitudinal axis of the femoral bone tunnel and therefore the direction of approach from such portals to the femoral bone tunnel to insert a bone screw is angularly offset also. The femoral bone tunnel opens on the femoral condyle at a site near the attachment site of the cruciate ligament. Longitudinal alignment of the screw driver with the opening of the femoral bone tunnel on the femoral condyle is difficult using conventional surgical drivers when the approach is made through the arthroscopic portals. This in turn presents difficulties in driving the screw parallel with the longitudinal axis of the femoral bone tunnel and the bone block in the tunnel.

Attempting to force the driver into parallelism with the longitudinal axis of the femoral bone tunnel runs a number of serious risks, including the possible breakage of the shaft of the driver at the knee: disengagement of the bone screws from the driver during manipulation and their contact with adjacent knee structures, followed by loss of the bone screw in the knee; and misalignment of the bone screw between the wall of the femoral bone tunnel and the bone block.

One compromise approach to the problem of location of arthroscopic portals is to introduce additional portals specifically for the purpose of inserting bone screws into the bone tunnel. One approach is to insert the bone screw through openings of the femoral bone tunnels on the lateral femoral cortex via portals placed proximally and laterally on the patients' thigh. This approach precludes the use of blind or closed end femoral bone tunnels. Alternatively, bone screws can be inserted through openings in the femoral condyle after their introduction through the tibial bone tunnels. In this case, the knee is hyperflexed to longitudinally align the tibial bone tunnel with the femoral bone tunnel, and hyperflexion must be maintained until the ligament is fixated in the femoral bone tunnel.

Angled drivers have been used in industrial applications as wrenches and screw drivers, and exemplary of such devices are U.S. Pat. Nos. 4,643,052 to Badiali, 4,620,458 to Schmidek, 3,788,169 to Nakayama, 3,696,694 to Boro, 3,232,151 to Blachowski, 2,042,376 to Balga, 1,428,282 to Glabaznya, 1,398,116 to Root, 2,199,823 to Sadtler, 933,639 to Frink and 877,571 to Larson. In medical applications, angled drivers have been used in power tools such as drills, and U.S. Pat. Nos. 5,041,119 to Frigg et al and 4,947,942 to Lightle et al are illustrative of angled, surgical power drills.

Prior art angled surgical drivers are unsuitable for use in least invasive, or endoscopic, surgical procedures to insert bone screws in bone tunnels directly from portals not aligned parallel with longitudinal axes of the bone tunnels. Moreover, angled surgical drivers in the prior art cannot effectively hold screws captive for insertion into the body through endoscopic size portals.

SUMMARY OF THE INVENTION

The present invention provides an improved method of cruciate ligament reconstruction that is less invasive and that reduces the risk of failure in comparison to existing methods. This method in accordance with a preferred embodiment of the present invention involves forming a portal in tissue adjacent to the joint to allow access for visualizing the joint by arthroscopy. The same portal is then used to insert an instrument to form a bone tunnel having a longitudinal axis in a bone of the joint at a site near the site of the ligament attachment. A ligament having a bone block at each end is then positioned to extend across the joint with the bone block disposed in the bone tunnel. A surgical screw driver bearing a bone screw is introduced into the joint from a portal formed in tissue adjacent to the joint and not aligned with the direction of insertion. The bone screw is placed in the correct position in the bone tunnel by the surgical screw driver, which drives the bone screw in a direction of insertion parallel with the longitudinal axis of the bone tunnel between the tunnel wall and the bone block to fixate the ligament. The second end of the ligament is similarly fixated to another bone of the joint.

In a preferred embodiment of the invention, the femoral bone tunnel is closed-ended. The bone screw is inserted into the femoral bone tunnel from an opening of the bone tunnel at the femoral condyle and a ligament is fixated with the bone screw with the knee positioned substantially at a 90 degree angle.

In an alternative embodiment of the invention, the bone screws are inserted from anterolateral and anteromedial portals through an open-ended femoral tunnel.

In another embodiment, the present invention provides an angled surgical screw driver for driving bone screws into bone so that the screw is securely supported by the driver until insertion has been completed. Angled surgical screw drivers have not previously been designed for use in arthroscopic cruciate ligament reconstruction of the knee to insert bone screws in bone tunnels in directions parallel with walls of the bone tunnels and bone blocks in the bone tunnels while approaching the bone tunnels from portals offset from the directions of screw insertion, and this embodiment permits the bone screw to be inserted, via the driver, deeper into a bone tunnel than would be possible with conventional screw drivers. It also permits access from an arthroscopic portal not aligned parallel with a longitudinal axis of the bone, to tunnel and to place the bone screw parallel with the walls of the bone tunnel and the bone block while driving the screw from a direction angularly disposed with the tunnel wall.

The embodiment has an operating shaft, a sleeve concentrically disposed around the operating shaft, a handle mounting the operating shaft for rotation relative to the sleeve, a drive head, angularly mounted on the operating shaft, which rotates in response to rotation of the operating shaft, and a drive head housing mounting ends of the drive head and the operating shaft.

The handle includes a static handle section securing an end of the sleeve and a rearward movable handle section securing an end of the operating shaft. An indicator on the handle allows orientation of the drive tip to be identified externally of the body, when the drive tip is inserted in the body through portals of minimal size. A socket having a hexagonal configuration in cross-section is formed in the operating shaft. A ball with a hexagonal configuration in cross-section corresponding to the configuration of the socket is provided on the drive shaft for engaging the socket. The drive shaft is mounted on the operating shaft at an angle of approximately 20° with respect to the longitudinal axis of the operating shaft and, therefore, the angled driver.

The drive shaft has a drive tip to engage a drive recess of a bone screw, to permit rotation of the screw about the longitudinal axis of the drive shaft.

A retaining mechanism for holding a bone screw captive on the drive shaft prior to screw insertion includes a wire having a proximal cylindrical section secured in a passage in the drive tip aligned with the longitudinal axis of the drive shaft and a distal cylindrical section that protrudes beyond the drive tip to be received in the cannula of the bone screw. The distal cylindrical section of the retaining mechanism is formed with a thermally set, slight curve or kink to hold the screw temporarily in place on the drive tip.

The procedure in accordance with a preferred embodiment of the present invention eliminates the step of penetrating the lateral femoral cortex and permits a countersink of the screw below the opening of the femoral bone tunnel on the femoral condyle. The procedure can be performed with fewer and smaller portals. In fact, the anteromedial and anterolateral portals formed for procedures preparatory to graft fixation can be utilized to directly insert bone screws in femoral bone tunnels. In addition, hyperflexion of the knee in arthroscopic anterior cruciate ligament reconstruction can be eliminated.

The surgical instrument provided in a preferred embodiment of the invention is designed to avoid drive shaft breakage, loss of bone screws at the knee joint, and to enhance screw insertion and driver positioning. In addition, screw divergence is minimized and maximum thread purchase along the length of the bone block is ensured. The embodiment is of unified construction for easy cleaning and sterilization with right and left knee compatibility. The embodiment employs a lightweight, ergonomic handle providing a balanced feel for the surgeon. Friction between relatively movable components of the handle is minimized to provide good tactile response,

BRIEF DESCRIPTION OF THE DRAWINGS

These and other features of the present invention may be more readily understood by reference to the following description, taken in conjunction with the accompanying drawings, in which.

DESCRIPTION OF SPECIFIC EMBODIMENTS

Figure 1:
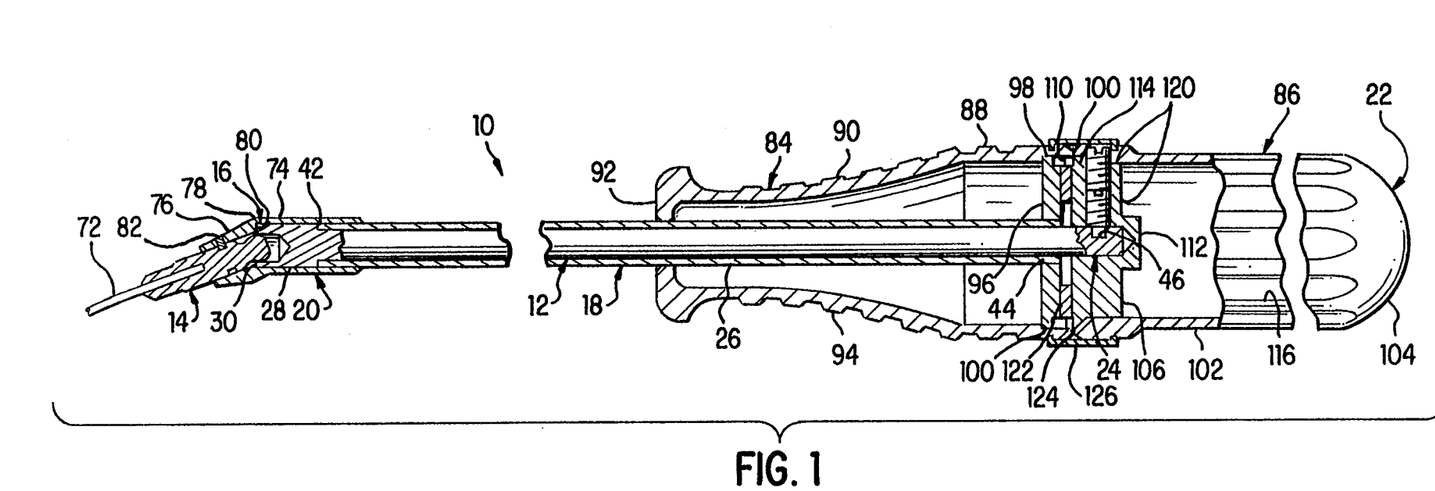
FIG. 1 is a broken side view, partly in longitudinal section, of a preferred embodiment of an angled surgical screw driver according to the present invention.

An angled surgical screw driver 10 according to a preferred embodiment of the present invention is illustrated in FIG. 1, and includes an elongate operating shaft 12 with a distal end 16 coupled to a drive shaft 14 and a proximal end 24 on which is mounted a movable portion of handle 22. Concentrically disposed around the operating shaft 12 is a sleeve 18, having a distal end 42, on which is mounted a drive head housing 20 and a proximal end 44 secured in a fixed portion of handle 22. Turning the movable portion of handle 22 with respect to the fixed portion thereof causes rotation of the drive shaft 14, which is disposed at an angle of approximately 20° from the axis of rotation of handle 22. The operation of the screw driver 12 is described in further detail below.

Figure 2:
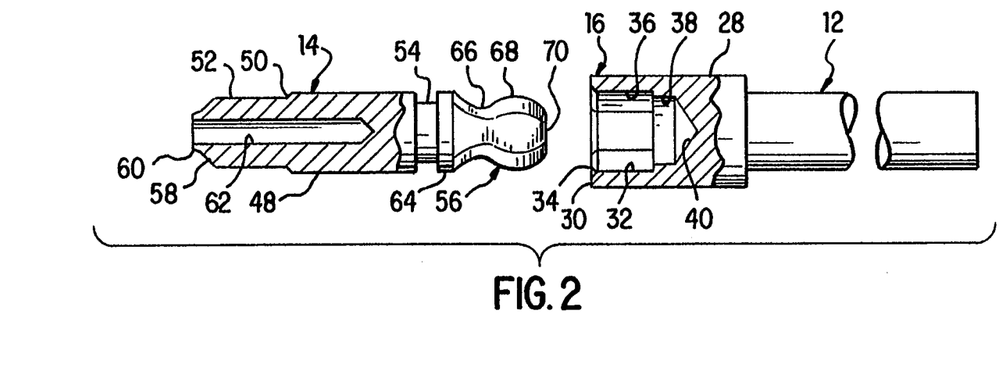
FIG. 2 is an exploded, broken side view, partly in section, of the distal end of the angled surgical screw driver of FIG. 1.

The operating shaft 12 is preferably made of stainless steel with a cylindrical body terminating, at the distal end 16, at a distal end wall 30. Fitted concentrically around the distal end 16 is a cylindrical barrel 28, detail of which is shown in FIG. 2. A socket 32 is formed distally in barrel 28 in axial alignment with a longitudinal axis of the operating shaft 12 and, therefore, the longitudinal axis of the driver 10, as shown in FIGS. 1 and 2.

Socket 32 includes successively a tapered distal recess 34 at end wall 30, an intermediate recess 36, having a hexagonal configuration in cross-section, a cylindrical recess 38, and a conical proximal recess 40. The recesses are contiguous. Intermediate recess 36 is formed of six flat sides extending longitudinally in the barrel 28 from distal recess 34 to cylindrical recess 38. The cylindrical recess 38 has a diameter smaller than the diametric, cross-sectional dimension of the intermediate recess 36.

A ball mechanism 56 includes a cylindrical flange 64 joined to cylindrical neck 54, a curved neck 66 extending proximally from flange 64, and a ball 68 mounted on curved neck 66. The cylindrical flange 64 has an outer diameter that is substantially the same as the outer diameter of the cylindrical body 48 and larger than the diameter of the cylindrical neck 54, such that an annular recess is defined concentrically around the cylindrical neck 54 laterally between the body 48 and the flange 64 of the drive shaft 14. The ball 68 has a hexagonal configuration in cross-section, being formed of six curved surfaces extending proximally from curved neck 66 to an end surface 70. Ball 68 is configured to be received in socket 32 of the operating shaft 12 with the longitudinal axis of the drive shaft 14 disposed at an acute angle of approximately 20° with respect to the longitudinal axis of the operating shaft 12. Engagement of the ball 68 in the socket 32 causes rotation of the drive shaft 14 in response to rotation of the operating shaft 12.

Drive shaft 14 is preferably made of stainless steel and, as shown in FIGS. 1 and 2, includes a cylindrical body 48, a drive tip 52, and the ball mechanism 56, in axial alignment. The cylindrical body 48 is joined to the drive tip 52 at the distal end of a shoulder 50 tapered in a distal direction, the proximal end of shoulder 50 joining a neck 54, which in turn proximally joins the cylindrical body 48 to the ball mechanism 56. The drive tip 52 has a distally tapered shoulder 58 terminating distally at an annular, peripheral lip 60, and a cylindrical passage 62 is formed in the drive tip 52 to extend proximally, longitudinally from lip 60 in axial alignment with the longitudinal axis of the drive shaft.

One purpose of the drive tip 52 is to frictionally secure the end of a length of guide wire 72, such as a nitinol wire, as will be explained below, as shown in FIG. 1. Another purpose of the drive tip is to frictionally engage a bone screw. The drive tip 52 has an external configuration to frictionally engage a drive recess 143 of an interference bone fixation screw 144. The drive tip 52 can have various cross-sectional configurations—for example, multi-lobed or pronged, or hexagonal—corresponding to the configuration of the drive recess 143 of the fixation screw 144, so the screw will be rotated in bone with rotation of the drive shaft 14.

The cylindrical body 48 may be formed with the same cross-sectional configuration as, but slightly greater dimensions than, the drive tip 52, so as to frictionally engage the drive recess 143 of the screw 144, when, as shown in FIG. 1, the drive tip 52 is inserted deeply enough into the screw 144 to cause the body 48 portion to enter the drive recess 143.

In a preferred embodiment, the drive shaft 14 is prevented from being inserted into the drive recess 143 so far that the drive head housing 20 contacts the proximal end of screw 144. In this embodiment, the back end of the bone screw 144 is spaced distally from the drive head housing 20 to allow a portion (approximately 5 mm in one preferred embodiment) of the drive shaft 14 beyond the drive head housing 20 to be exposed. The exposed portion permits the bone screw 144 to be countersunk into a bone tunnel by an approximate additional amount equal to the length of the exposed portion.

The back end of the bone screw can be made to terminate distally of the drive head housing 20 in various ways. These include (a) making the distance from the lip 60 to the drive head housing 20 less than the length of the drive recess 143; or (b) forming the drive shaft 14 with external configurations or diametric dimensions limiting the distance that the drive shaft 14 can be inserted in the drive recess 143; or (c) providing a retaining mechanism on the drive shaft 14 that limits the distance that the drive shaft 14 can be inserted in the drive recess 143 as will be explained further below.

Drive head housing 20 is preferably made of stainless steel and includes a cylindrical section 74 and a distally tapered nose section 76 joined to the cylindrical section 74 at a bend 78, the nose section 76 extending angularly, distally from the cylindrical section 74. The wall of the cylindrical section 74 has a thickness that is substantially constant along the length of the cylindrical section with an inner diameter sized to closely receive the outer diameters of the cylindrical barrel 28 and the sleeve 18. The wall of the nose section 76 has a thickness that is greater than the wall thickness of the cylindrical section 74 at bend 78 to define an internal shoulder 80 serving as a stop for cylindrical barrel 28 when operating shaft 12 is disposed within the cylindrical section 74. The wall thickness of the nose section 76 tapers in a distal direction such that an internal, cylindrical passage of substantially constant cross-section is defined along the length of the nose section. The cylindrical passage of the nose section 76 is disposed at an angle with respect to the longitudinal axis of the cylindrical passage of the cylindrical section 74 that the angle of the drive shaft 14 with respect to the operating shaft 12.

A C-shaped clip 82 is mounted (by welding, for example, or simply by appropriate dimensions) in an annular slot in the nose section 76 and is received in the annular recess around neck 54 to prevent axial movement of the drive shaft 14 while allowing the drive shaft to rotate within the housing 20.

Figure 4:
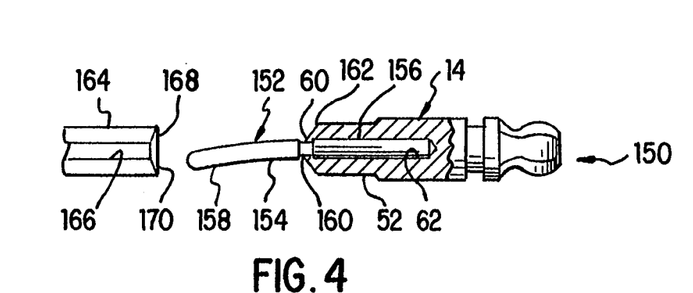
FIG. 4 is a broken side view, partly in section, of the drive shaft of a related embodiment of an angled surgical screw driver according to the present invention, showing a retaining mechanism on the drive shaft and an end of a forming tool for mounting the retaining mechanism on the drive shaft.
Figure 6:
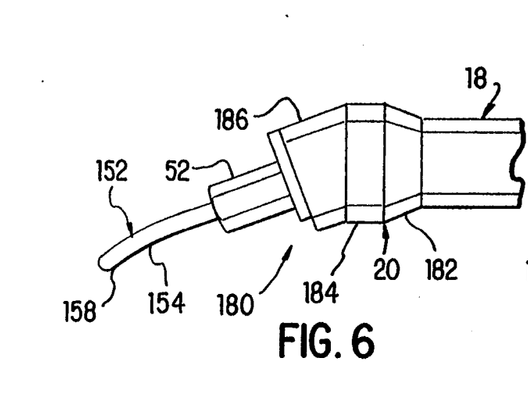
FIG. 6 is a broken side view of the distal end of a further embodiment of an angled surgical screw driver according to the present invention, showing a bone screw mounted on the screw driver.
Figure 8:
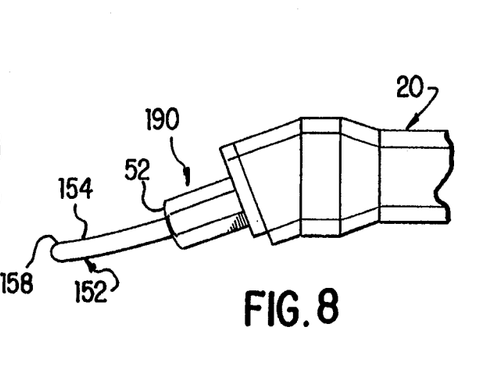
FIG. 8 is a broken side view of the distal end of another embodiment of an angled surgical screw driver according to the present invention, showing a bone screw mounted on the screw driver.

In a related embodiment of the angled surgical screw driver according to the present invention, shown in FIGS. 4, 6 and 8, the angled driver 150 is substantially the same as the angled driver 10 of FIG. 1, except that a retaining mechanism 152, for holding an interference bone fixation screw captive on the driver prior to insertion of the screw, is mounted on drive shaft 14. Retaining mechanism 152 includes a length of wire 154 (identified in FIGS. 6 and 8), such as a nitinol wire, having a proximal cylindrical section 156, which is joined to neck 160 at a shoulder 162, and a distal cylindrical section 158 joined to the proximal cylindrical section 156 by neck 160.

The neck 160 has an outer diameter that is smaller than the outer diameters of the proximal and distal cylindrical sections, which in turn are slightly smaller than the diameter of the cannula 145 in the interference bone fixation screw 144. The outer diameter of the proximal cylindrical section 156 is sufficient to be received in the passage 62 in the drive tip 52 of drive head 14. The distal cylindrical section 158 is formed with a thermally set, slight radius curve along its length. The length of the wire 154 that protrudes beyond the drive tip 52 when the proximal cylindrical section 156 is received therein is selected to allow the curved distal cylindrical section 158 to be disposed in the cannula 145 of the screw 144 and to provide frictional engagement with the walls forming the cannula 145 when the screw is placed upon the drive shaft 14, such as shown in FIG. 8.

The wire 154 is mounted on the drive shaft 14 by press fitting the proximal cylindrical section 156 in the passage 62 of the drive tip 52 in a manner such that the neck 160 is aligned with edge 60 of drive tip 52. In some instances, depending on the material from which tip 152 is made, a press fit is sufficient and there is no need for neck 160 or shoulder 162. In other instances, when a neck and shoulder structure is used, a forming tool 164 is useful.

Forming tool 164 has a longitudinal cavity 166 terminating at a recess 168 tapered in the distal direction. In use, the forming tool 164 is moved along the wire 154 in the direction of the drive shaft 14 until the end wall 170 abuts the drive tip 52. In that position, the forming tool is urged against the tip 52, and the forming tool's tapered recess 168 forces the lip 60 to grip neck 160, and this grip, along with the shoulder 160, prevent the wire 154 from falling out of the drive shaft 14.

The retaining mechanism 152 may be used on drivers having drive tips axially aligned with longitudinal axes of the drivers to hold a bone screw upon the drivers prior to screw insertion, and the retaining mechanism 152 is not limited to use with angled drivers. The retaining mechanism 152 may also be constructed in such a way that the fit of the wire 154 in the cannula 145 of screw 144 limits the depth that the drive shaft 14 may be inserted into the drive recess 143.

The proximal end 24 of the operating shaft 12 extends beyond the proximal end 44 of the sleeve 18. A cylindrical aperture 46 to receive a set screw is formed in the proximal extension and is disposed radially with respect to the longitudinal axis of the operating shaft 12.

The sleeve 18 has an outer diameter substantially the same as the outer diameter of barrel 28 at the distal end of the sleeve to form a smooth external profile with the barrel. The sleeve 18 has an inner diameter sized to closely receive the outer diameter of the operating shaft 12 while still permitting the operating shaft 12 to rotate relative to the sleeve 18.

Handle 22 is preferably made of stainless steel and includes a forward static handle section 84, securing sleeve 18, and a rearward movable handle section 86, rotatable relative to the forward section 84.

Forward handle section 84 is of hollow construction and has a cylindrical wall 88 defining an open proximal end and a tapered wall 90 distally joined to cylindrical wall 88 and terminating at a front wall 92. Wall 90 is tapered in a distal direction and is flared adjacent to front wall 92 to define an external profile that facilitates grasping during use. Concentric ribs 94 are provided along an external surface of the forward handle section 84 to facilitate gripping during use. A cylindrical bushing 96 is disposed in the open proximal end of the forward handle section 84. The bushing 96 has an annular, peripheral flange 98 at a forward face thereof abutting an internal annular shoulder 100 of the cylindrical wall 88. A central opening is formed in bushing 96 for securing the proximal end 44 of the sleeve 18 therein. Bushing 96 and sleeve 18 are preferably welded to the forward handle section 84 to form a sealed, water-tight cavity.

Rearward handle section 86 is of hollow construction, having a cylindrical wall 102 defining an open distal end that is closed by end cap 104. A cylindrical bushing 106 is disposed in the open distal end of the rearward handle section 86. The bushing 106 has an annular, peripheral flange 108 at a forward face thereof, and annular rim 110, extending axially in a direction distal from the flange 108, and a central, cylindrical protrusion 112 extending in a proximal direction. The bushing 106 is axially in disposed in the open face front end of the rearward handle section 86 with flange 108 abutting an internal shoulder 114 of cylindrical wall 102. An axial cavity is formed in bushing 106, extending proximally from the forward face thereof into the protrusion 112, for mounting the proximal end 24 of the operating shaft 12. Bushing 106 is preferably welded to the rearward handle section 86 to form a sealed, watertight cavity. Longitudinal ridges 116 are provided along an external surface of the rearward handle section 86 to facilitate gripping during use. A pair of set screws 120 is used to couple the rearward handle section 86 to the operating shaft 12. The screws are disposed in a cylindrical passage formed in the bushing 106, radially disposed with respect to the longitudinal axis of the operating shaft 12 and in communication with the axial cavity of the bushing, the cylindrical passage being aligned with an opening in the cylindrical wall of 102 of the rearward handle section 86.

The forward handle section 84 is assembled with the rearward handle section 86, in such a way that the cylindrical wall of 88 within the distal end of the forward handle section 84 abuts the cylindrical wall 102 of the rearward handle section 86 at a junction 124. A ring 126, preferably made of stainless steel, is disposed concentrically around the handle 22 to extend over the junction 124, the ring 126 being mounted in grooves in the forward and rearward handle sections, while creating a stainless to stainless bearing surface that minimizes friction between the relatively movable components of the handle 22, to provide a good tactile response during use. A thrust washer 122 is disposed concentrically within rim 110 abutting the forward face of the bushing 106 such that the rearward handle section 86 can be assembled with the forward handle section 84 with the thrust washer 122 abutting a rearward face of bushing 96 and rim 110 extending along the cylindrical wall 88 within the distal end of the forward handle section 84.

Handle 22 is of lightweight, ergonomic construction to provide a balanced feel for a surgeon during use. During use, upon rotation of the rearward handle section 86 relative to the forward handle section 84, the operating shaft 12 will be rotated relative to sleeve 18, causing rotation of drive shaft 14 and the drive tip 52.

Figure 3:
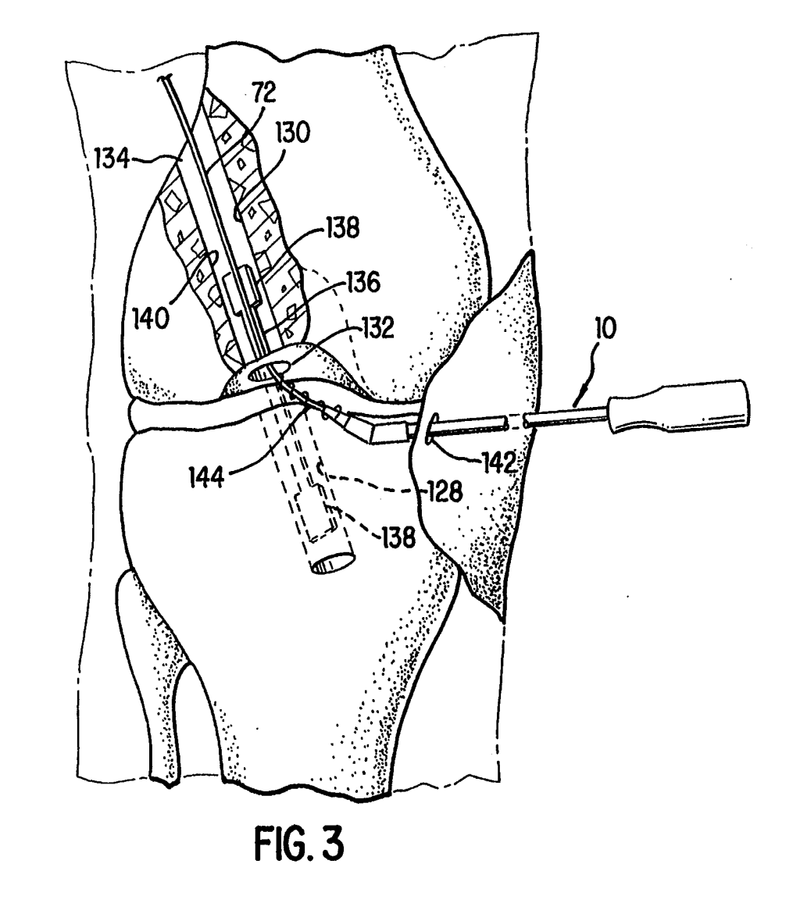
FIG. 3 is a front view, partly in section, of the joint of a right knee positioned at substantially 90°, showing the angled surgical screw driver of FIG. 1 approaching an open end femoral bone tunnel via an anterolateral portal.
Figure 3A:
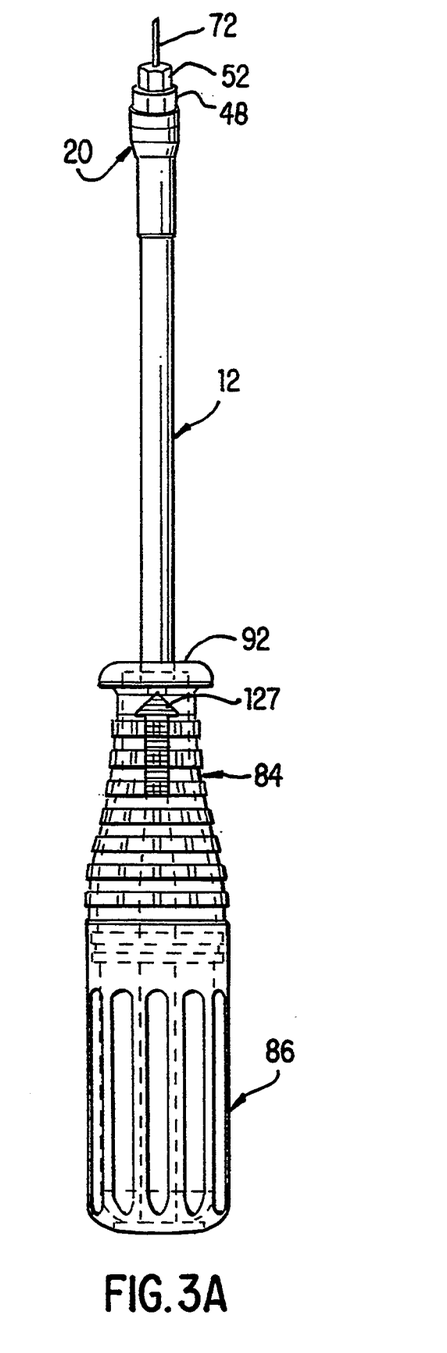
FIG. 3A is a top view of the angled surgical screw driver of FIG. 1.

As shown in FIG. 3A, indicator 127, here an arrow is provided along an external surface of the forward handle section 84 to indicate, from a position external of the body, the orientation of the drive tip 52 when inserted in the body through an endoscopic portal. The indicator 127 is disposed on the same side of handle 22 as the drive tip 52 and is aligned with the drive tip 52 and the longitudinal axis of the surgical screw driver 10 such that, with the indicator 127 facing a surgeon, the drive tip 52 will be oriented in a direction angularly upward relative to the longitudinal axis of the surgical screw driver. The indicator 127 may utilize a wide range of suitable symbols, including arrows, lines or dots, and may be formed on the handle in diverse ways, such as by laser etching, engraving, or chemical deposition.

Where formed as an indentation in the surface of the forward handle section 84, the indicator 127 can provide a tactile, as well as a visual, indication of the position of the drive tip 52.

The angled driver of the embodiment described herein includes numerous design features that facilitate its use in arthroscopic anterior cruciate ligament reconstruction. At the drive tip, the walls of the cylindrical section 74 and the nose section 76 have a minimal thickness to reduce the overall outer diameter of the angled surgical screw driver 10 in the area of bend 78, and the distance that the angled surgical screw driver 20 protrudes distally beyond bend 78 is minimized to enhance maneuverability of the driver within the close confines of the knee joint and to allow the use of smaller portals in arthroscopic cruciate ligament reconstruction. The minimal diametric dimension and distal taper of the nose section facilitate insertion of the driver in bone tunnels, allowing the drive shaft 14 to be inserted in bone tunnels up to bend 78. Shoulders 50 and 58 give the drive head 14 a distal taper, facilitating insertion in portals of minimal size and additionally enhance maneuverability at the knee joint. The drive shaft 14 protrudes beyond the back end of the bone screw 144 and spaces the bone screw distally from the bend 78 a greater amount, such that the bone screw can be inserted that much further into a bone tunnel with the driver inserted in the bone tunnel up to the bend 78. According to a preferred embodiment, the outer diameter of the angled driver 10 at bend 78 is approximately 0.350 inches (8.9 mm), and the distance that the driver protrudes distally of bend 78 is approximately 0.710 inches (18.0 mm).

The surgical screw driver of the present invention is useful for arthroscopic ligament reconstruction procedures of the knee and of other joints in the human body. The knee is an example of a moveable joint that sustains injury to connective tissue with relative frequency. Although the surgical screw driver is described herein as applicable to methods of anterior cruciate ligament reconstruction, the surgical screw driver according to the present invention can also be used in reconstructing posterior ligaments of the knee. Other joints also rely on Ligaments to maintain function. In all joints, ligaments play an important role in holding the different bones of the joints in alignment.

A method of least invasive, or arthoscopic, anterior cruciate ligament reconstruction according to the present invention is shown in FIG. 3. An incision of minimal size is made medial to the tibial tubercle and distal to the joint line to harvest a portion of the patellar tendon which will serve as a graft ligament. Subsequently, this incision can be utilized as the portal 142 for inserting surgical instruments to fix one end of the graft ligament in the femoral bone tunnel as described below, and may also be used for access to the region of the cruciate ligament attachment sites to help determine proper placement of the tibial and femoral bone tunnels, with the knee being visualized with an arthroscope.

Tibial bone tunnel 128 and femoral bone tunnel 130 are formed respectively in the tibia and femur. The femoral bone tunnel is formed by instruments inserted in a cephalad direction through the tibial bone tunnel. The femoral bone tunnel 130 is formed as an open-ended longitudinally straight, cylindrical tunnel extending from an opening 132 on the femoral condyle at the attachment site of the anterior cruciate ligament on the femur to an opening 134 on the lateral femoral cortex with (in one embodiment of the method) soft tissue covering the lateral femoral cortex remaining intact. The central longitudinal axis of the femoral bone tunnel is therefore substantially offset from the portal 142.

A ligament 136, such as a prosthetic ligament or the graft ligament harvested as previously described, having bone blocks 138 or other suitable terminus at its ends, is inserted initially in the tibial bone tunnel 128 in the femoral bone tunnel 130 via a puncture wound. (The puncture wound is in line with opening 134 on the lateral femoral cortex and forward proximally and laterally on the patient's thigh.) The ligament 136 is then positioned so as to extend across the knee joint with a bone block 138 or other terminus positioned in each of the bone tunnels 128 and 130.

A guide wire is utilized to insert the ligament 136 and thereafter to guide a bone screw positioned on a driver to the bone block at the end of the graft ligament for the purposes of securing the ligament with the screw. The guide wire 72 is made from a material such as a nitinol wire and is typically on the order of 14 inches in length. It is inserted into the tibial bone tunnel 128 and through the femoral tunnel 130, with the guide wire 72 exiting the knee through the soft tissue adjacent the lateral femoral cortex. Alternatively, the guide wire 72 can be inserted through the opening 134 on the lateral femoral cortex via the puncture wound described previously.

Following insertion of the ligament 136, the guide wire 72 is positioned in the femoral bone tunnel 130 laterally between the bone block 138 and a wall 140 of the femoral bone tunnel, to be disposed parallel with the bone block 138 and the wall 140 and, therefore, parallel with the central longitudinal axis of the femoral bone tunnel. The guide wire 72 is advanced through the puncture wound until an end of the guide wire 72 is visible at the knee joint. The visible end of the guide wire is grasped and disposed externally of the knee, creating a substantial bend in the guide wire 72, as shown in FIG. 3, using an instrument which is inserted through an anteromedial or anterolateral portal, such as anterolateral portal 142 formed in tissue adjacent the knee joint. The bend in the guide wire is due to the fact that the portal 142 is substantially offset from, and not aligned with, the central longitudinal axis of the femoral bone tunnel 130. A bone screw 144 having a cannula 145, in the form of a central, coaxial, longitudinal passage therein, is mounted on the end of the guide wire 72 externally of the knee, the cannula having a diameter slightly larger than the diameter of the guide wire 72. The end of the guide wire 72 is frictionally secured in the cylindrical passage 62 of the drive tip 52. The bone screw 144 is moved along the guide wire and mounted on the drive tip 52 by drive recess 143. Since the drive recess is coaxial with the cannula, the drive shaft 14 protrudes from the back end of the bone screw 144 by about 5 mm.

With the knee at an angle of substantially 90°, the angled screw driver 10 is inserted at the knee joint via the portal 142. The driver is guided into the femoral bone tunnel 130 through the opening 132 on the femoral condyle by simultaneously turning and pushing the driver with the drive tip 52 oriented upwardly. The orientation of the drive tip is indicated by the indicator 127 on the forward handle section facing the surgeon, as shown in FIG. 3A. The direction of insertion from the portal 142 to the femoral bone tunnel 130 is at a non-zero acute angle with respect to the central longitudinal axis of the femoral bone tunnel because the portal 142 is not aligned with the femoral bone tunnel axis. The angled screw driver 10, as guided by the guide wire 172, is moved forward along the femoral bone tunnel 130, with the longitudinal axis of the drive shaft 14 disposed parallel with the longitudinal axis of the femoral bone tunnel; and, concurrently, the guide wire 72 is pushed cephalad in the tunnel and through the puncture wound.

Once the tip of the bone screw 144 is disposed adjacent the bone block 138, the rearward handle section 86 of the angled screw driver is manually rotated relative to the forward handle section 84, while the forward handle section is grasped and held fixed, to rotate the operating shaft 12 relative to the sleeve 18. Consequently, the drive shaft 14 (the driven end), driven by handle 22, drives the screw 144 in a direction that is at a non-zero acute angle with respect to the handle (i.e., the driving end) of the angled screw driver. Accordingly, the bone screw 144 is driven in a forward direction in the femoral bone tunnel 130 laterally between the bone block 138 and the wall 140 and parallel to the bone block 138 and the wall 140. A thread on the screw engages the tunnel wall 140 and the bone block 138 along the length of the bone block to fixate the ligament 136. The bone screw is driven externally of the knee from a direction offset from the direction of bone screw insertion and with the knee at an angle of substantially 90° such that the hyperflexion is avoided. The bone screw 144 is driven an additional 5 mm into the femoral bone tunnel 130 due to the exposed portion of the drive shaft 14 at the back end of the screw, allowing a countersink below the opening 132.

The angled screw driver 10 is then pulled away from the screw 144 for removal through portal 142, and the guide wire 72 can be removed with the driver 10 or pulled away from the driver 10 for removal via the puncture wound in the soft tissue adjacent the lateral femoral cortex. The bone block 138 in the tibial bone tunnel 128 is then fixated by inserting a bone screw in the tibial bone tunnel and driving the bone screw parallel to the bone block and a wall of the tibial bone tunnel.

It will be appreciated that portal 142 can be the same portal utilized for alignment determination in forming the tibial and femoral bone tunnels, and that a single portal can be used throughout the procedure to harvest the patellar tendon graft, to orient the tibial and femoral bone tunnels, to help orient the graft ligament, and to insert the bone screw in the femoral bone tunnel.

It will also be appreciated that the drive shaft 14 of the surgical screw driver can be offset from the handle 22 by the bend 78 or a curve as well as other configurations and that the bend, curve or other configuration can be rigid or flexible. The angled surgical screw driver 10 can be used with or without the guide wire 72.

Figure 5:
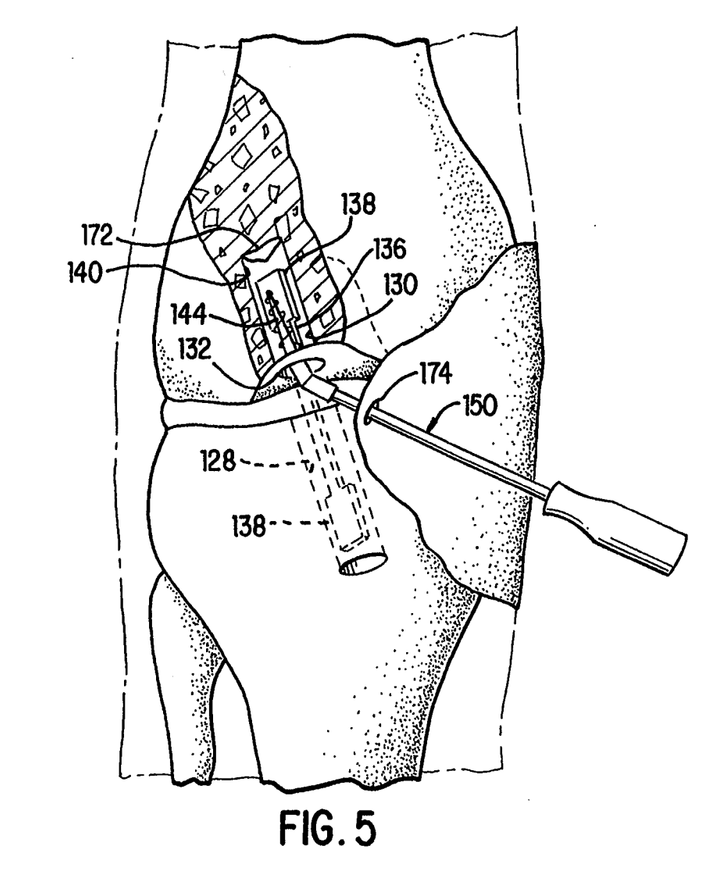
FIG. 5 is a front view, partly in section, of the knee, joint of a right knee positioned at substantially 90°, showing the angled surgical screw driver of FIG. 4 inserting a bone screw in a closed end femoral bone tunnel via an anteromedial portal.

A related embodiment of the method of arthroscopic, anterior cruciate ligament reconstruction according to the present invention is shown in FIG. 5. Instead of the femoral bone tunnel being formed as an open-ended tunnel, the femoral bone tunnel 130 is formed as a blind, or closed-ended tunnel extending from an opening 132 on the femoral condyle to an end wall 172 such that the femoral bone tunnel does not broach the lateral femoral cortex.

A graft or prosthetic ligament 136 having bone blocks 138 at its ends is inserted in the tibial bone tunnel 128 via the portal to extend across the knee joint with a bone block 138 disposed in each of the bone tunnels of the femur and the tibia.

A bone screw 144 is mounted on the angled screw driver 150 externally of the knee. The drive tip 52 of the driver is engaged in the drive recess of the screw and the retaining mechanism 152 is received in the cannula of the screw. In this configuration, the drive shaft 14 protrudes beyond the back end of the screw 144 substantially 5 mm. The curve of the distal cylindrical section 158 of the wire 154 provides frictional engagement in the cannula of the screw 144. The screw is positively held by the retaining mechanism 152 upon the angled driver 150 prior to screw insertion. This arrangement allows manipulation of the screw at the knee joint while avoiding disengagement of the screw from the driver and possible loss of the screw in the knee.

With the knee at an angle of substantially 90°, the angled driver 150 with the screw 144 held thereon by retaining mechanism 152 is inserted at the knee joint via an anteromedial or anterolateral portal, such as anteromedial portal 174. The driver and screw are guided into the femoral bone tunnel 130 through the opening 132 on the femoral condyle. The drive tip 52 remains pointed upwards as indicated by indicator 127 facing the surgeon. The direction of insertion from the portal 174 to the femoral bone tunnel 130 is at a non-zero acute angle with respect to the central longitudinal axis of the femoral bone tunnel. The angled driver 150 is advanced along the femoral bone tunnel 130 in a direction parallel with the bone block 138 and the wall 140, and therefore, parallel with the longitudinal axis of the femoral bone tunnel until the bone screw 144 is positioned laterally between the bone block 138 and a wall 140 of the femoral bone tunnel as shown in FIG. 5.

Once the tip of the bone screw 144 is disposed adjacent the bone block 138, the rearward handle section 86 of the angled driver 150 is rotated relative to the forward handle section 84 while the forward handle section 86 is held fixed, to drive the bone screw 144 into the femoral bone tunnel 130 as described in connection with FIG. 3, and to fixate the ligament 136. Again the longitudinal axis of the operating shaft 12 is angularly disposed with respect to the direction of insertion. The screw is inserted an additional 5 mm into the femoral bone tunnel 128 and driven parallel with the bone block 138 in the tibial bone tunnel.

As in the case of FIG. 3, portal 174 can be the same portal as utilized in orienting the tibial and femoral bone tunnels, and a single portal can be used to harvest the patellar tendon graft, to orient the tibial and femoral bone tunnels, and to fixate the ligament in the femoral bone tunnel.

A guide wire can be used with the angled driver 150 by being driven into the femur to guide the driver during screw insertion. Such a guide wire can be used with the retaining mechanism 152, or in place of the retaining mechanism 152, or as a retaining mechanism by lengthening the distal cylindrical section 158.

Figure 7:
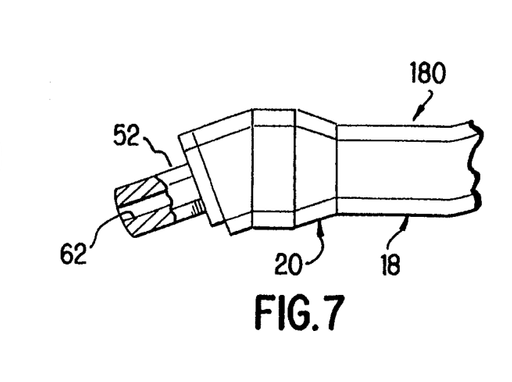
FIG. 7 is a broken side view, partly in section, of the drive shaft for the angled surgical screw driver of FIG. 6.

A related embodiment of an angled driver according to the present invention is shown at the distal end in FIGS. 6 and 7 as item 180, which is similar to the angled driver 150, and includes a drive head housing 20 mounting the drive shaft and a distal end of the operating shaft, the drive shaft including a drive tip 52 having a hexagonal configuration in cross-section for engaging a hexagonal drive recess 143 of an interference bone fixation screw 144.

Drive head housing 20 of angled driver 180 is formed integrally with sleeve 18 and includes a flared section 182 distally joined to the sleeve 18, an intermediate cylindrical section 184 joined to flared section 182 and an angled section 186 joined to intermediate section 184. The flared and intermediate sections 182 and 184 are axially aligned, while the angled section 186 is angularly offset from the flared and intermediate sections such that a longitudinal axis of the angled section is disposed at an angle, with respect to a longitudinal axis of the flared and intermediate sections, that is substantially the same as the angle that the longitudinal axis of the drive shaft is disposed with the longitudinal axis of the operating shaft.

The drive tip 52 of the angled driver 180 is formed of six facets for engaging the drive recess 143 of the bone screw 144. Drive tip 52 can have a configuration in cross-section that is substantially constant along the length of the drive tip as shown in FIG. 6, or the drive tip 52 can be tapered or stepped in a distal direction to further facilitate insertion through very small portals and mobility at the knee joint. It includes a cylindrical passage 62 coaxial with the drive shaft as shown in FIG. 7, for securing retaining mechanism 152. Retaining mechanism 152 includes a wire 154 press fit into passage 62 and having a distal cylindrical section 158 protruding beyond the drive tip 52. The distal cylindrical section 158 is formed with a thermally set, angled bend along a longitudinal axis of the wire 154, the bend being offset from the longitudinal axis of the drive shaft for being disposed in the cannula 145 of the bone screw 144. The bone screw is mounted on drive tip 52 such that the screw will be forced slightly out of axial alignment with the drive tip 52 to produce frictional engagement of the drive tip in the drive recess of the screw to resist disengagement of the screw from the angled driver prior to screw insertion as shown in FIG. 6.

A further modification of an angled driver according to the present invention is shown in FIG. 8 at 190, in which the bone screw is mounted on drive tip 52 without forcing the screw out of axial alignment with the drive tip. In all other respects, angled driver 190 is substantially the same as angled driver 180.

Both angled driver 180 and 190 can be utilized for insertion of bone screws, in arthroscopic cruciate ligament reconstruction in bone tunnels from directions offset from the direction of screw insertion and from portals not aligned with the bone tunnels as previously described; and, the angled screw driver 180 can be used with or without a guide wire.

The angled screw driver and methods of arthroscopic cruciate ligament reconstruction of the knee according to the present invention allow bone screws to be inserted in bone tunnels parallel with walls of the bone tunnels and bone blocks in the bone tunnels to obtain maximum thread purchase along the entire length of the bone blocks with the screws being driven from directions offset from the direction of screw insertion. Bone screws can be inserted in femoral bone tunnels directly from anteromedial or anterolateral portals and without accessing the femoral bone tunnels through the tibial bone tunnels. For example, bone screws can be inserted in the femoral bone tunnels with the knee positioned at an angle of substantially 90°. The present invention removes the undesirable requirement for hyperflexion of the knee in order to insert bone screws.

In addition, the same portal can be employed to perform procedures preparatory to graft fixation, to orient the tibial and femoral bone tunnels and to insert interference bone fixation screws in the femoral bone tunnel, thereby eliminating the need for portals in soft tissue adjacent the lateral femoral cortex specifically formed for the purpose of inserting bone screws in the femoral bone tunnel. Using the methods of this invention, trauma and invasiveness are minimized.

A retaining mechanism according to the present invention can be provided on the surgical screw driver to hold the interference bone fixation screw captive upon the driver prior to screw insertion while avoiding breakage of the driver at the knee joint. This retaining mechanism prevents disengagement of the screw from the driver and possible loss of the screw at the knee joint.

By minimizing the outer diameter of the drive shaft and operating shaft, smaller portals can be used in arthroscopic cruciate ligament reconstruction; and, by forming the drive shaft to be stepped or tapered in a distal direction, easy insertion of the angled driver through smaller portals is insured. By minimizing the outer diameter of the drive head housing and the length of the driver that extends distally beyond the operating shaft, greater maneuverability and mobility of the angled driver at the knee joint is afforded.

With a portion of the drive shaft exposed beyond the back end of a bone screw, the bone screw can be inserted deeply in a bone tunnel with the angled surgical screw driver of the present invention.

The surgical screw driver and its method of use described above for anterior cruciate ligament reconstruction of the knee can also be applied to other ligament reconstruction procedures including arthroscopic posterior cruciate ligament reconstruction of the knee. In the latter case, the driver provides a means to insert bone screws in bone tunnels in a direction parallel with walls of the bone tunnels and bone blocks in the bone tunnels to fixate a graft or prosthetic ligament in the anatomic position of the posterior cruciate ligament while introducing the screws through portals not aligned with the direction of screw insertion.

The angled driver and method of arthroscopic anterior cruciate ligament reconstruction according to the present invention permit blind, or closed end, femoral bone tunnels that do not broach the lateral femoral cortex to be utilized in arthroscopic anterior cruciate ligament reconstruction such that trauma and invasiveness are minimized.

Further details concerning practice of the present invention are described by David A. McGuire, M.D., an inventor herein, in the brochure entitled "The Paramex to ACL Guide System Surgical Techniques", and incorporated herein by reference (published by Linvatec Corporation, Largo, Fla. 34643) submitted herewith.

Inasmuch as the present invention is subject to many variations, modifications and changes in detail, it is intended that the subject matter discussed above and shown in the accompanying drawings may be interpreted as illustrative not in a limiting sense.

What is claimed is:

1. A method for arthroscopic ligament reconstruction in a joint of the body:
    (a) forming in a bone of the joint a bone tunnel having a central longitudinal axis;
    (b) positioning a ligament having a terminus at each end so that a first terminus is disposed in the tunnel;
    (c) introducing a surgical screw driver from a portal that is substantially offset from the central longitudinal axis;
    (d) inserting an interference bone fixation screw in the bone tunnel with the surgical screw driver and driving the interference bone fixation screw to fixate the first terminus within the bone tunnel; and
    (e) fixating the second terminus to another bone of the joint.

2. A method of arthroscopic ligament reconstruction according to claim 1, wherein step (c) includes introducing at the joint from a portal the surgical screw driver along a direction of insertion that is disposed at a non-zero acute angle with respect to the central longitudinal axis of the bone tunnel.

3. A method of arthroscopic ligament reconstruction according to claim 2, wherein step (a) includes the step of inserting an arthroscope through a portal that is the same one as used in step (c).

4. A method according to claim 1, wherein the screw driver has driving and driven ends each with an axis, with the driving end's axis disposed at a non-zero acute angle with respect to the axis of the driven end.

5. A method of arthroscopic ligament reconstruction according to claim 4, wherein the step of driving in step (d) includes driving the screw in the bone tunnel in a direction of insertion parallel with the central longitudinal axis of the bone tunnel with the axis of the driving end disposed at a non-zero acute angle with respect to the bone tunnel's central longitudinal axis.

6. A method of arthroscopic ligament reconstruction according to claim 4, wherein the joint is the knee and the reconstruction is of a cruciate ligament.

7. A method of arthroscopic ligament reconstruction according to claim 6, wherein the bone tunnel is a femoral bone tunnel, and step (a) includes forming the femoral bone tunnel near the attachment site of a cruciate ligament.

8. A method of arthroscopic ligament reconstruction according to claim 7, wherein step (b) includes inserting a ligament having bone blocks at its ends and positioning the ligament to extend across the knee joint with a bone block disposed in the femoral bone tunnel.

9. A method of arthroscopic ligament reconstruction according to claim 8, wherein the portal is an anteriomedial portal.

10. A method of arthroscopic ligament reconstruction according to claim 9, wherein the portal is disposed medially with respect to the tibial tubercle and distally with respect to the joint line.

11. A method of arthroscopic ligament reconstruction according to claim 10, further comprising the steps of forming a tibial bone tunnel and fixating the ligament in the tibial bone tunnel.

12. A method of arthroscopic ligament reconstruction according to claim 10, wherein step (c) is conducted with the knee positioned at an angle of approximately 90°.

13. A method of arthroscopic ligament reconstruction according to claim 8, wherein the portal is an anteromedial portal.

14. A method of arthroscopic ligament reconstruction according to claim 7, comprising prior to step (c), the steps of inserting in the femoral bone tunnel a guide wire disposed laterally between the bone block bone tunnel and the wall of the bone tunnel and parallel with the longitudinal axis of the femoral bone tunnel, positioning an end of the guide wire at the knee joint, inserting an instrument at the knee joint through the portal and grasping the end of the guide wire with the instrument to pull the guide wire externally of the knee joint through the portal and positioning the bone screw upon the guide wire.

15. A method of arthroscopic ligament reconstruction according to claim 14, wherein the bone screw includes a cannula and the step of positioning the bone screw includes positioning the guide wire to extend through the cannula in the bone screw.

16. A method of arthroscopic ligament reconstruction according to claim 15, wherein the bone screw includes a drive recess and the step of inserting the surgical screw driver in step (d) includes securing the guide wire, with the bone screw positioned thereon, in the driven end of the driver externally of the knee, and engaging the driven end of the driver in the drive recess of the bone screw.

17. A method of arthroscopic ligament reconstruction according to claim 16, wherein the driven end includes a longitudinal passage and the step of securing the guide wire includes securing the guide wire in the longitudinal passage of the driven end.

18. A method of arthroscopic ligament reconstruction according to claim 7, wherein the step of forming includes forming the femoral bone tunnel to extend from the opening on the femoral condyle to an end wall within the femur.

19. A method of arthroscopic ligament reconstruction according to claim 7, wherein the driven end includes a retaining mechanism, the method further comprising prior to step (c), placing the bone screw upon the retaining mechanism to create a friction fit resisting disengagement of the bone screw from the drive shaft.

20. A method of arthroscopic ligament reconstruction according to claim 19, wherein the bone screw includes a cannula and the retaining mechanism includes a wire having a distal section formed with a curve protruding from the drive shaft of the driver and the step of placing the bone screw includes placing the distal section within the cannula of the bone screw to create a friction fit in the cannula of the screw.

21. A method of arthroscopic ligament reconstruction according to claim 19, wherein the bone screw includes a cannula and the retaining mechanism includes a wire having a distal section formed with a bend angularly offset from the longitudinal axis of the driven end and protruding from the driven end of the driver and the step of placing the bone screw includes placing the distal section within the cannula of the bone screw to force the bone screw out of axial alignment with the driven end to create a friction fit between the driven end and the screw.

22. A method of arthroscopic ligament reconstruction according to claim 4, wherein the surgical screw driver includes a handle having a static handle section and a movable handle section and the step of driving includes rotating the movable handle section of the handle relative to the static handle section externally of the knee to rotate the driven end in response to rotation of the movable handle section.

* * * * *